US012616602B2

(12) United States Patent
Sileika et al.

(10) Patent No.: US 12,616,602 B2
(45) Date of Patent: May 5, 2026

(54) BACTERIA FORMULATION AND PRODUCTS INCLUDING SAME

(71) Applicant: Hollister Incorporated, Libertyville, IL (US)

(72) Inventors: Tadas S. Sileika, Lake Forest, IL (US); Mark W. Jockel, Vernon Hills, IL (US); Nicole L. Dean, Antioch, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 560 days.

(21) Appl. No.: 18/004,933

(22) PCT Filed: Aug. 4, 2021

(86) PCT No.: PCT/US2021/044457
§ 371 (c)(1),
(2) Date: Jan. 10, 2023

(87) PCT Pub. No.: WO2022/031788
PCT Pub. Date: Feb. 10, 2022

(65) Prior Publication Data
US 2023/0301816 A1     Sep. 28, 2023

Related U.S. Application Data

(60) Provisional application No. 63/062,013, filed on Aug. 6, 2020.

(51) Int. Cl.
*A61F 5/441*      (2006.01)
*A61K 8/99*       (2017.01)
(Continued)

(52) U.S. Cl.
CPC ................ *A61F 5/441* (2013.01); *A61K 8/99* (2013.01); *A61K 35/74* (2013.01); *A61K 35/741* (2013.01);
(Continued)

(58) Field of Classification Search
CPC ........... A61F 5/441; A61K 8/99; A61K 35/74; A61K 35/741; A61K 2035/115; A61P 31/04; A61Q 15/00
See application file for complete search history.

(56) References Cited

U.S. PATENT DOCUMENTS 4,211,224 A     7/1980   Kubach
4,490,145 A     12/1984  Campbell
(Continued)

FOREIGN PATENT DOCUMENTS

CN     107400649 A     11/2017
CN     109734263 A  *  5/2019
(Continued)

OTHER PUBLICATIONS

International Search Report issued by ISA/EPO in connection with PCT/US2021/044457 dated Jan. 4, 2022.
(Continued)

*Primary Examiner* — Sarah Al Hashimi
*Assistant Examiner* — Hans Kaliher
(74) *Attorney, Agent, or Firm* — Klintworth & Rozenblat LLP

(57) ABSTRACT
A bacteria formulation includes bacteria including odor neutralizing bacteria configured to oxidize hydrogen sulfide and/or methyl mercaptan and one or more compounds for supporting viability of the bacteria.

14 Claims, 1 Drawing Sheet

(51) Int. Cl.

| | | |
|---|---|---|
| *A61K 35/00* | (2006.01) | |
| *A61K 35/74* | (2015.01) | |
| *A61K 35/741* | (2015.01) | |
| *A61P 31/04* | (2006.01) | |
| *A61Q 15/00* | (2006.01) | |

(52) U.S. Cl.

CPC .............. *A61P 31/04* (2018.01); *A61Q 15/00* (2013.01); *A61K 2035/115* (2013.01); *A61K 2800/77* (2013.01)

(56) References Cited

U.S. PATENT DOCUMENTS

| | | | |
|---|---|---|---|
| 5,411,496 | A | 5/1995 | Homa |
| 5,496,396 | A | 3/1996 | Allan et al. |
| 5,860,959 | A | 1/1999 | Gent |
| 6,129,716 | A * | 10/2000 | Steer ....................... A61F 5/441 604/338 |
| 6,165,159 | A | 12/2000 | Blanton |
| 6,410,305 | B1 * | 6/2002 | Miller ..................... C02F 3/342 435/856 |
| 6,432,093 | B1 | 8/2002 | Shiina |
| 6,656,169 | B1 | 12/2003 | Steer |
| 9,259,512 | B2 | 2/2016 | Udayakumar et al. |
| 2006/0228323 | A1 | 10/2006 | Novelle |
| 2007/0060900 | A1 | 3/2007 | Maurer et al. |
| 2011/0038919 | A1 | 2/2011 | Tauer et al. |
| 2012/0207811 | A1 | 8/2012 | Tauer et al. |
| 2013/0035653 | A1 | 2/2013 | Kannankeril et al. |
| 2013/0096521 | A1 | 4/2013 | Bekele |
| 2016/0333348 | A1 * | 11/2016 | Clube ....................... C12N 9/16 |
| 2017/0095431 | A1 * | 4/2017 | Andrews .............. A61K 9/7084 |
| 2019/0365560 | A1 * | 12/2019 | Timms ...................... A61L 9/01 |
| 2020/0297619 | A1 * | 9/2020 | Ambrogio .............. A61Q 19/10 |
| 2022/0304843 | A1 * | 9/2022 | Menifee .................. A61F 5/441 |

FOREIGN PATENT DOCUMENTS

| | | | |
|---|---|---|---|
| EP | 1510244 | B1 | 1/2008 |
| JP | H08107927 | A * | 4/1996 |
| WO | 20080019887 | A2 | 2/2008 |
| WO | 20080100993 | A1 | 8/2008 |

OTHER PUBLICATIONS

Written Opinion of the International Searching Authority issued by ISA/EPO in connection with PCT/US2021/044457 dated Jan. 4, 2022.

Kanagawa Takahiro et al: "Removal of methanethiol, dimethyl sulfide, dimethyl disulfide and hydrogen sulfide from contaminated air by Thiobacillus thioparus TK-m", Applied and Environmental Microbiology, vol. 55, No. 3, Mar. 1, 1989, pp. 555-558.

Cha J. et al: "Removal of organo-sulphur odour compounds by Thiobacillus novellus SRM, sulphur-oxidizing microorganisms", Process Biochemistry, vol. 34, Jan. 1, 1999, pp. 659-665.

Talaiekhozani Amirreza et al: "An overview of principles of odor production, emission, and control methods in wastewater collection and treatment systems", Journal of Environmental Management, vol. 170, Jan. 30, 2016, pp. 186-206.

Syed, M. et al, "Removal of hydrogen sulfide from gas streams using biological processes—A review", Canadian Biosystems Engineering, vol. 48, 2006.

Brinkhoff, T. et al. "*Thiomicrospira kuenenii* sp. nov. and *Thiomicrospira frisia* sp. nov., two mesophilic obligately chemolithoautotrophic sulfu-roxidizing bacteria isolated from an intertidal mud flat", International Journal of Systematic Bacteriology (1999), 49, 385-392.

Kelly, D. et al. "Proposal for the reclassification of *Thiobacillus novellus* as *Starkeya novella* gen. nov., comb. nov., in the a-subclass of the Proteobacteria", International Journal of Systematic and Evolutionary Microbiology (2000), 50, 1797-1802.

Kelly, D. et al. "Confirmation of *Thiobacillus denitrificans* as a species of the genus *Thiobacillus*, in the b subclass of the Proteobacteria, with strain NCIMB 9548 as the type strain" International Journal of Systematic and Evolutionary Microbiology (2000), 50, 547-550.

Odintsova, E. et al. "*Themothrrjc azorensis* sp. nov., an Obligately Chemolithoautotrophic, Sulfur-Oxidizing, Thermophilic Bacterium" International Journal of Systematic Bacteriology, Apr. 1996, p. 422-428.

Soreanu, G. et al. "Laboratory pilot scale study for H2S removal from biogas in an anoxic biotrickling filter", Water Science & Technology, 57.2, 2008.

Sorokin, D. et al. "*Thioalkalispira microaerophila* gen. nov., sp. nov., a novel lithoautotrophic, sulfur-oxidizing bacterium from a soda lake", International Journal of Systematic and Evolutionary Microbiology (2002), 52, 2175-2182.

Takano, B. et al. "Influence of Sulfur-Oxidizing Bacteria on the Budget of Sulfate in Yugama Crater Lake, Kusatsu-Shirane Volcano, Japan", Biogeochemistry, vol. 38, No. 3 (Sep. 1997), pp. 227-253.

Vlasceanu, L. et al. "Characterization of Thiobacillus thioparus LV43 and Its Distribution in a Chemoautotrophically Based Groundwater Ecosystem", Applied and Environmental Microbiology, Aug. 1997, p. 3123-3127.

Chung, Y. et al. "Operation optimization of Thiobacillus thioparus CHI 1 biofilter for hydrogen sulfide removal", Journal of Biotechnology 52 (1996) 31-38.

Kim, H. et al. "Long-Term Operation of a Biofilter for Simultaneous Removal of H2S and NH3", Journal of the Air & Waste Management Association; Dec. 2002; 52, 12; ProQuest p. 1389.

Kleerebezem, R. et al. "Autotrophic denitrification for combined hydrogen sulfide removal from biogas and post-denitrification", Water Science and Technology vol. 45 No. 10 pp. 349-356.

Lampe, D. et al. "Evaluation of Sulfur-Based Autotrophic Denitrification", Department of Civil Engineering, University of Nebraska-Lincoln at Omaha Campus, Omaha, NE, 68182-0178.

McComas, C et al. "Characterization of a Novel Biocatalyst System for Sulfide Oxidation", Biotechnol. Prog. 2001, 17, 439-446.

Mesa, M. et al. "Biological iron oxidation by Acidithiobacillus ferrooxidans in a packed-bed bioreactor", Chem. Biochem. Eng. Q. 16 (2) 69-73 (2002).

Basu, R. et al. "Biological Conversion of Hydrogen Sulfide into Elemental Sulfur", Environmental Progress (vol. 15, No. 4), Winter, 1996.

Nelson, D. et al. "Use of Reduced Sulfur Compounds by *Beggiatoa* sp.", Journal of Bacteriology, Jul. 1981, p. 140-154, vol. 147, No. 1.

Pinjing, H. et al. "Removal of hydrogen sulfide and methyl mercaptan by a packed tower with immobilized micro-organism beads", Water Science and Technology vol. 44 No. 9 pp. 327-333, 2001.

Haukioja, A. "Probiotics and Oral Health", European Journal of Dentistry, Jul. 2010—vol. 4.

Keller, M. et al. "Effect of chewing gums containing the probiotic bacterium *Lactobacillus reuteri* on oral malodour", Acta odontologica Scandinavica • Dec. 2011.

Iwamoto, T. et al. "Effects of probiotic Lactobacillus salivarius WB21 on halitosis and oral health: an open-label pilot trial", OOOOE Journal, Aug. 2010.

Alok, A. et al. "Probiotics: A New Era of Biotherapy", Advanced Biomedical Research, Jun. 31, 2017.

Donohue, D. et al. "Safety of pro biotic bacteria", Asia Pacific J Clin Nutr (1996) 5: 25-28.

International Preliminary Report on Patentability issued by WIPO in connection with PCT/US2021/044457 dated Feb. 16, 2023.

* cited by examiner

BACTERIA FORMULATION AND PRODUCTS INCLUDING SAME

This is a National Stage Application of International Patent Application No. PCT/US2021/044457 filed Aug. 4, 2021, which claims the benefit of and priority to U.S. Provisional Application No. 63/062,013 filed Aug. 6, 2020, the entirety of which are incorporated fully herein by reference.

BACKGROUND

The following description relates generally to bacteria formulations, and in particular, to odor neutralizing and probiotic bacteria formulations which may be used, for example, in medical products such as ostomy pouch systems and skin contacting adhesives.

An ostomy pouch system typically includes a pouch formed from opposing sidewalls defining an internal collection area, an inlet opening for receiving a stoma, and an ostomy appliance for attaching the pouch to a user. The ostomy appliance may include, for example, an ostomy barrier of a one-piece pouch system, which is attached to one of the pouch sidewalls proximate an inlet opening, a faceplate for a two-piece pouch system configured to releasably engage a pouch, and a barrier ring. The ostomy appliance may include a skin barrier material for adhering to and sealing against user's peristomal skin surrounding the stoma.

Ostomy pouch systems may produce odors from stomal effluent stored in the ostomy pouch. The odors may be vented from the ostomy pouch to the atmosphere. It is desirable to neutralize or minimize odors associated with use of the ostomy pouch system. To this end, an ostomy pouch may include a filter configured to deodorize gas vented from the pouch. In addition, body odors may be produced at an interface of a skin contacting surface of a medical product and the user's body as a result of moisture between the skin contacting surface and the user's body. Further, a user may be susceptible to skin infections where the skin contacting surface contacts the skin.

Conventional ostomy pouch filters may be relatively expensive and may not deodorize vented gas sufficiently. As a result, odors associated with vented gas may be detected by the user or others in the vicinity of the user. In addition, a user may attempt to minimize body odors by frequent cleansing and replacement of products having skin contacting surfaces. However, frequent cleansing may be tedious, time consuming, and cause skin irritation. Frequent replacement of products having skin contacting surfaces may result in inefficient use of the products. Skin infections may lead to user discomfort and may cause complications.

Accordingly, it is desirable to provide an odor neutralizing bacteria formulation and an odor neutralizing and probiotic bacteria formulation which may be used with medical products such as ostomy pouch systems or skin contacting adhesives.

SUMMARY

In one aspect, a bacteria formulation includes bacteria including odor neutralizing bacteria configured to oxidize hydrogen sulfide and/or methyl mercaptan, and one or more compounds for supporting viability of the bacteria.

In an embodiment, the odor neutralizing bacteria may be chemotrophic bacteria. The odor neutralizing bacteria may be one or more of: *Thiobacillus* sp., *Thiobacillus denitrifi-*

*cans, Thiobacillus ferrooxidans, Thiobacillus thiooxidans, Thiobacillus novellus, Thiobacillus thioparus, Thermothrix azorensis, Thiothrix nivea, Thioalkalispira microaerophila* and *Thiomicrospira frisia.* In an embodiment, the one or more compounds may include one or more of a nutrient, a buffering agent and/or a supplement.

In an embodiment, the bacteria formulation may further include photosynthetic bacteria. In an embodiment, the bacteria formulation may further include *Beggiatoa* spp.

In an embodiment, the bacteria may further include probiotic bacteria for providing an antimicrobial effect. The probiotic bacteria may be one or more of: *Lactobacillus* spp, *Lactococcus, Leuconostoc, Bifidobacterium* and *Saccharomyces.*

In an embodiment, the bacteria and the one or more compounds may interact to provide pH in a range of about 2-3. In an embodiment, the bacteria and the one or more compounds may interact to provide pH in a range of about 6-8.

In another aspect, an ostomy system includes an ostomy pouch having opposed sidewalls forming an enclosed area configured to receive and store stomal effluent and a pouch filter connected to one of the sidewalls. The ostomy system further includes an ostomy appliance configured to be adhered to a user's skin, and a bacteria formulation having bacteria including odor neutralizing bacteria and one or more compounds for supporting viability of the bacteria.

In an embodiment, the bacteria formulation may be disposed in the enclosed area of the ostomy pouch. In an embodiment, the pouch filter may include the bacteria formulation. In an embodiment, the pouch filter does not include activated carbon.

In an embodiment, the bacteria may further include probiotic bacteria for providing an antimicrobial effect. In an embodiment, the ostomy pouch may include a pouch film which includes the bacteria formulation. In an embodiment, the ostomy pouch may include a comfort panel which includes the bacteria formulation. In an embodiment, the ostomy appliance may include a skin contacting adhesive which includes the bacteria formulation.

In an embodiment, the odor neutralizing bacteria may be one or more of: *Thiobacillus* sp., *Thiobacillus denitrificans, Thiobacillus ferrooxidans, Thiobacillus thiooxidans, Thiobacillus novellus, Thiobacillus thioparus, Thermothrix azorensis, Thiothrix nivea, Thioalkalispira microaerophila* and *Thiomicrospira.* In an embodiment, the probiotic bacteria may be one or more of: *Lactobacillus* spp, *Lactococcus, Leuconostoc, Bifidobacterium* and *Saccharomyces.*

In another aspect, an ostomy pouch includes opposed sidewalls forming an enclosed area configured to receive and store stomal effluent, a pouch filter connected to one of the sidewalls, the pouch filter configured for venting gas or evaporated stomal effluent from the enclosed area to the atmosphere. The ostomy pouch further includes a bacteria formulation having bacteria including odor neutralizing bacteria and one or more compounds for supporting viability of the bacteria.

In an embodiment, the bacteria formulation may be disposed in the enclosed area of the ostomy pouch. In an embodiment, the pouch filter may include the bacteria formulation. In an embodiment, the pouch filter does not include activated carbon.

In an embodiment, the bacteria may further include probiotic bacteria for providing an antimicrobial effect. In an embodiment, the ostomy pouch may further include a pouch film which includes the bacteria formulation. In an embodiment, the ostomy pouch may further include a comfort panel which includes the bacteria formulation.

In another aspect, an ostomy appliance includes a skin contacting adhesive including a bacteria formulation having bacteria including odor neutralizing bacteria and probiotic bacteria, and one or more compounds for supporting viability of the bacteria.

In another aspect, an ostomy pouch filter includes a filter element including a bacteria formulation having bacteria including odor neutralizing bacteria and one or more compounds for supporting viability of the bacteria.

In an embodiment, the filter element may include a first section and a second section and the bacteria formulation may include a first bacteria formulation and a second bacteria formulation. In an embodiment, the first bacteria formulation may be configured to provide pH in a range of about 2-3 and the second bacteria formulation may be configured to provide pH in a range of about 6-8. In an embodiment, the first bacteria formulation may be configured to convert hydrogen sulfide to a neutralized variant and the second bacteria formulation may be configured to convert methyl mercaptan to a neutralized variant. In an embodiment, the filter element does not include activated carbon.

In another aspect, a skin contacting adhesive of a medical product includes a skin contacting adhesive material including a bacteria formulation having bacteria including odor neutralizing bacteria and probiotic bacteria, and one or more compounds for supporting viability of the bacteria.

In another aspect, a skin fold management fabric includes a fabric material including a bacteria formulation having bacteria including odor neutralizing bacteria and probiotic bacteria, and one or more compounds for supporting viability of the bacteria.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
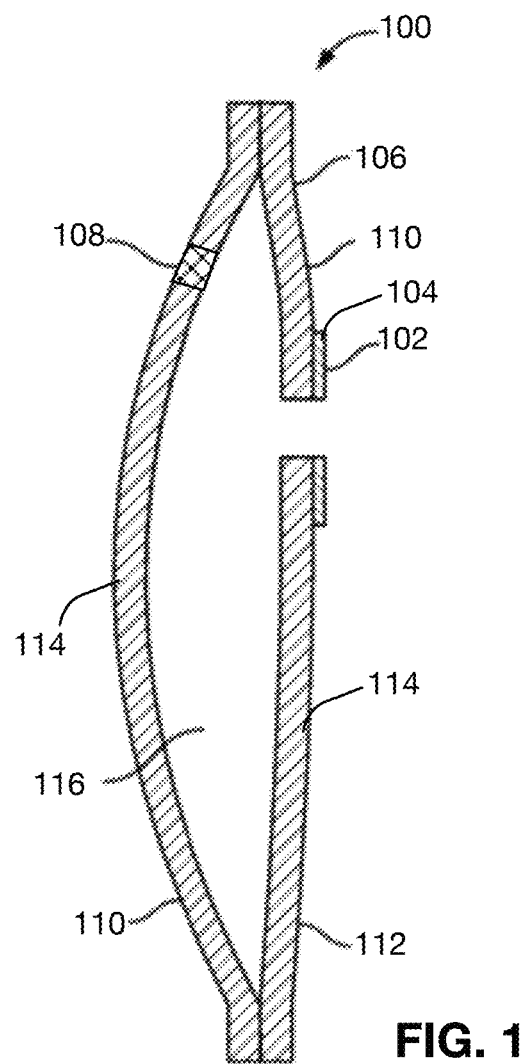
FIG. 1 is a cross-sectional illustration of an ostomy pouch according to an embodiment of the present disclosure.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

In embodiments herein, a bacteria formulation may be configured to neutralize odor and/or provide antimicrobial effects. For example, the bacteria formulation may be an odor neutralizing bacteria formulation and may oxidize hydrogen sulfide (H2S), methyl mercaptan (CH4S), other odorous gasses, and/or other odorous liquids. Alternatively, the bacteria formulation may be an odor neutralizing and probiotic bacteria formulation, which in addition to neutralizing odors, such as body odor, may offer protection against pathogens, and thus, may inhibit skin infections such as bacterial infections, fungal infections and/or yeast skin infections.

In an embodiment, the bacteria formulation may include bacteria. The bacteria may include the odor neutralizing bacteria, the probiotic bacteria, or both. For example, the odor neutralizing bacteria formulation may include the odor neutralizing bacteria. The odor neutralizing and probiotic bacteria formulation may include the odor neutralizing bacteria and the probiotic bacteria.

The bacteria formulation may also include one or more compounds for supporting viability of the bacteria when in situ in an environment for use. The one or more compounds may include, for example, nutrients, buffering agents and/or supplements. The nutrients may be potential nutrients for the bacteria and may include, for example, sugars, peptides, amino acids and other known, suitable nutrients. The buffering agents may help control pH of the resultant compounds that are excreted by the bacteria, such as sulfuric acid, after degradation of hydrogen sulfide and methyl mercaptan. The supplements may include, for example, an iron supplement to serve as an elemental energy source, depending on the particular bacteria used.

In an embodiment, the bacteria formulation may be provided as a powder, a tablet, a capsule, dissolvable pouch, microbead or the like. For example, the bacteria formulation may be provided as a package in the form of a powder, a tablet, a capsule, a dissolvable pouch, a microbead or other similar, suitable package, including combinations of these examples. In an embodiment, the package may be a layer of material and the bacteria formulation may be embedded in or on the material. In an embodiment, the bacteria may be spun or wound into selected products. In an embodiment, a microbead may be formed by blending bacteria and the one or more compounds. In an embodiment, separate microbeads may be formed for different bacteria types (e.g., the odor neutralizing bacteria and the probiotic bacteria) or microbeads may be formed by blending different bacteria types together along with the one or more compounds.

In an embodiment, the package may be configured to substantially isolate the bacteria formulation from an environment until desired use of the bacteria formulation. The bacteria formulation may interact with the environment in response to the package being activated. For example, the package may include a membrane configured to contain the bacteria formulation. In an embodiment, the package may be divided into one or more compartments to separately store the bacteria and the one or more compounds, thereby substantially preventing interaction between bacteria and the one or more compounds before use.

The membrane may be activated in response to exposure to a predetermined environmental condition, reagent, catalyst or the like. For example, the membrane may be activated in response to exposure to an environmental condition such as a predetermined activation humidity, temperature, pressure, light and/or other environmental condition. The membrane may also be activated in response to exposure to a predetermined reagent or catalyst such as water or other liquid, stomal effluent, or other predetermined compound, mixture, chemical and the like. In an embodiment, activation of the membrane may cause the membrane to dissolve, tear, burst or otherwise allow for interaction between the environment and the bacteria formulation. Activation of the membrane may also allow interaction between bacteria and/or the one or more compounds stored in separate compartments of the package. In this manner, the bacteria and the one or more compounds may interact with one another and the environment to provide the odor neutralization and/or antimicrobial effects.

Figure 2:
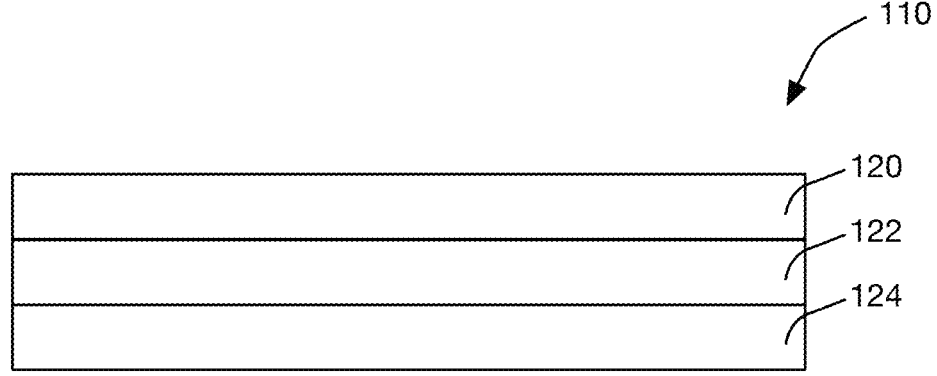
FIG. 2 is a cross-sectional illustration of a composite film that may comprise the ostomy pouch of FIG. 1.

Referring to FIGS. 1 and 2, the bacteria formulation may be added to or included in a medical product, such as an ostomy pouch system 100 or a skin contacting adhesive 102. The ostomy pouch system 100 may include, for example, an ostomy appliance 104, an ostomy pouch 106 and/or a pouch filter 108. The skin contacting adhesive 102 may be included with, for example, the ostomy appliance 104, wound care products, critical care products, temporary anchorage devices (TADs), patient monitoring applications and the like. The bacteria formulation may be added to other skin contacting medical products or components as well, such as skin fold management fabrics.

According to embodiments herein, the bacteria formulation may include odor neutralizing bacteria and may be added to an ostomy pouch 106. In another embodiment, bacteria formulation may include odor neutralizing bacteria and may replace activated carbon and potassium permanganate (KMnO4) in a pouch filter 108 and/or be added to a pouch filter 108 having activated carbon. In another embodiment, the bacteria formulation may include odor neutralizing bacteria and probiotic bacteria and may be added to an ostomy pouch film 110 and/or ostomy pouch comfort panel 112. In other embodiments, the bacteria formulation may include odor neutralizing bacteria and probiotic bacteria and may be added to skin contacting adhesives 102 and/or to skin fold management fabrics. The bacteria formulation may neutralize body odors and provide an antimicrobial effect to protect against pathogens, thereby inhibiting skin infections.

In an embodiment, the bacteria of the bacteria formulation may be dehydrated before use. The bacteria may be rehydrated and become reanimated or activated in response to exposure, for example, to environmental moisture, such as stomal effluent, water vapor, perspiration or moisture in a skin contacting adhesive. Alternatively, the bacteria of the bacteria formulation may be provided in a live form. In the live form, rehydration and reanimation are not necessary.

In an embodiment, an ostomy pouch system may generally include an ostomy pouch 106 and an ostomy appliance 102. In an embodiment, the ostomy pouch 106 may include opposed sidewalls 114 forming an enclosed area 116 therebetween to receive and store stomal effluent. In an embodiment, the sidewalls 110 may be a film or multilayer films. One example of a suitable multilayer film includes a seal layer 120, barrier layer 122 and a foam or non-woven layer 124 configured to contact a user's skin for comfort. A pouch filter 108 may be connected to a sidewall 110. The pouch filter may accommodate gas venting between the enclosed area 116 and external atmosphere.

The ostomy appliance 104 may comprise a skin barrier and may be configured as a faceplate assembly for a two-piece ostomy pouch system, an ostomy barrier for a one-piece ostomy pouch system, an ostomy skin barrier ring, and the like. The ostomy appliance may include, for example, a skin contacting adhesive 102 configured to adhere to the user's skin and seal around the stoma. In an embodiment, the skin contacting adhesive may include a hydrocolloid adhesive or other suitable medical grade adhesive. In an embodiment, the ostomy appliance may include an adhesive layer which includes the skin contacting adhesive.

In an embodiment, and as described above, the odor neutralizing bacteria may oxidize hydrogen sulfide (H2S), methyl mercaptan (CH4S), other odorous gases and/or other odorous liquids. In an embodiment, suitable odor neutralizing bacteria may include chemotrophic bacteria. Chemotrophic bacteria utilize carbon dioxide as a source of chemical energy by oxidizing reduced inorganics such as hydrogen sulfide. If reduced organic carbon sources are present in the environment, such as amino acids and glucose, chemotrophic bacteria can grow heterotrophically. That is, chemotrophic bacteria can utilize organic carbon for a carbon source and inorganic carbon as energy.

Examples of suitable odor neutralizing bacteria include, but are not limited to: *Thiobacillus* sp., *Thiobacillus denitrificans, Thiobacillus ferrooxidans, Thiobacillus thiooxidans, Thiobacillus novellus, Thiobacillus thioparus, Thermothrix azorensis, Thiothrix nivea, Thioalkalispira microaerophila* and *Thiomicrospra frisia*. In an embodiment, the odor neutralizing bacteria may be selected from the examples above for use in the bacteria formulation.

Reaction mechanisms, depending on species and strain (methyl mercaptan degradation achieved by same organisms) may be as follow:

*Thiobacillus thioparus:*

$2HS-+O2\rightarrow2S0+2OH-$ $2S0+3O2+2OH-\rightarrow2SO42-+2H+$ $H2S+2O2\rightarrow SO42-+2H+$

*Thiobacillus denitrificans:*

$3HS-+3.9NO3-+0.2NH4++HCO3-+1.7H+$
$\rightarrow CH1.8O0.5N0.2+1.9N2+3SO42-+2.3H2O$ $14.5HS-+5NO3-+0.2NH4++HCO3-+20.3H+$
$\rightarrow CH1.8O0.5N0.02+2.5N2+14.5S+27.4H2O$ $55S+20CO2+50NO3-+38H2O+4NH4+$
$\rightarrow4C5H7O2N+25N2+55SO42-+64H+$ $5HS-+8NO3-+3H+\rightarrow5SO42-+4N2+4H2O$

*Thiobacillus ferrooxidans:*

$2FeSO4+H2SO4+\frac{1}{2}O2\rightarrow Fe2(SO4)3+H2O$ $2FeS2+7.5O2+H2O\rightarrow Fe2(SO4)3+H2SO4$ In an embodiment, additional photosynthetic bacteria, such as *Chlorobium thiosulfatophilum,* may be utilized to convert hydrogen sulfide and carbon dioxide (in the presence of light) to elemental sulfur and hydrocarbon biomass, along with water. In such an embodiment, a light source may be included to provide light to facilitate the reaction. The light source may be a reusable light source.

In an embodiment, *Beggiatoa* spp. may also be utilized to achieve elemental sulfur outputs from thiosulfate starting compounds.

In an embodiment, optimal pH for removal of hydrogen sulfide is around 2-3 and for methyl mercaptan is around 6-8.

Accordingly, the bacteria formulation may be an odor neutralizing bacteria formulation. The odor neutralizing bacteria formulation may include odor neutralizing bacteria and one or more compounds for supporting viability of the odor neutralizing bacteria in situ with an environment in which the bacteria formulation is used. The odor neutralizing bacteria formulation may further include additional photosynthetic bacteria. The odor neutralizing bacteria formulation may further include *Beggiatoa* spp. In an embodiment, the odor neutralizing bacteria formulation may be configured to provide a pH in a range of about 2-3 for removal of hydrogen sulfide. In an embodiment, the odor neutralizing bacteria formulation may be configured to provide a pH in a range of about 6-8 for removal of methyl mercaptan.

In an embodiment, probiotic bacteria may be suitable for protecting against pathogens and inhibiting microbial infections, for example, skin infections. The probiotic bacteria may reduce available resources to pathogenic bacteria and yeast. The probiotic bacteria may also reduce available space for pathogenic bacteria and yeast. The probiotic bacteria may also produce antimicrobial compounds to kill pathogenic bacteria and yeast.

Examples of suitable probiotic bacteria include, but are not limited to: *Lactobacillus* spp, *Lactococcus, Leuconostoc, Bifidobacterium* and *Saccharomyces*. In an embodiment, the probiotic bacteria may be selected from these for use in the bacteria formulation.

Accordingly, a bacteria formulation may be an odor neutralizing and probiotic bacteria formulation. The odor neutralizing and probiotic bacteria formulation may generally be formed as the odor neutralizing bacteria formulation and further include the probiotic bacteria. Thus, in an embodiment, the odor neutralizing and probiotic bacteria formulation may include odor neutralizing bacteria, probiotic bacteria and one or more compounds for supporting viability of the odor neutralizing bacteria and/or the probiotic bacteria in situ with an environment in which the bacteria formulation is used. The odor neutralizing and probiotic bacteria formulation may further include additional photosynthetic bacteria. The odor neutralizing and probiotic bacteria formulation may further include *Beggiatoa* spp.

In an embodiment, the odor neutralizing bacteria and the probiotic bacteria may be provided together in a bacteria formulation and may be added to a medical product using the same techniques or any combination of techniques described above, for example, by using a particular package or combination of packages. The bacteria of the present embodiments may not be capable of forming spores.

According to an embodiment, a bacteria formulation, such as the odor neutralizing bacteria formulation, may be added directly to an ostomy pouch, for example, in the enclosed area. The bacteria formulation may be added, for example, by the manufacturer after manufacture of the ostomy pouch, or later, by a user, prior to using the ostomy pouch.

In an embodiment, the bacteria, such as the odor neutralizing bacteria, may be provided in a dehydrated form. The bacteria may be rehydrated and become reanimated, for example, in response to exposure to liquid stomal effluent. The stomal effluent may be liquid fecal waste.

The bacteria formulation may be provided or packaged, for example, as a powder, a tablet, a capsule, a dissolvable pouch or the like. The one or more compounds of the bacteria formulation may support viability of the bacteria in situ with the stomal effluent.

Accordingly, in an embodiment, a bacteria formulation, such as the odor neutralizing bacteria formulation, may be added to an ostomy pouch before use of the ostomy pouch. Dehydrated bacteria may become reanimated or activated when exposed to stomal effluent. The bacteria may deodorize ostomy pouch contents before the contents interact with the filter of the ostomy pouch. Thus, odors typically associated with ostomy pouch venting may be substantially neutralized or avoided.

In the manner above, an ostomy pouch system may be provided having a bacteria formulation, such as the odor neutralizing bacteria formulation. The bacteria formulation may be provided in the enclosed area of the ostomy pouch. The bacteria may oxidize hydrogen sulfide H2S, methyl mercaptan CH4S, and/or other odorous gases and/or liquids to deodorize the contents of the ostomy pouch before gas is vented from the ostomy pouch to the environment.

According to an embodiment, a bacteria formulation, such as the odor neutralizing bacteria formulation, may be added to an ostomy pouch filter. The pouch filter may be formed without activated carbon and potassium permanganate (KMnO4). In an embodiment, the bacteria formulation may be added, for example, by the manufacturer after manufacture of the pouch filter, or later, by a user, prior to using the pouch filter.

In an embodiment, bacteria, such as the odor neutralizing bacteria, may be provided in a dehydrated form. The bacteria may be rehydrated and become animated, for example, in response to exposure to gas or evaporated stomal effluent, including water vapor, flowing through the pouch filter.

The bacteria formulation may be provided or packaged, for example, as a microbead prior to incorporation into the pouch filter. In an embodiment, the bacteria and the one or more compounds may be blended together to form the microbeads. In an embodiment, the microbeads may be incorporated into a membrane of the pouch filter. Alternatively, or in addition, the bacteria formulation may be spun or woven into layers of the pouch filter. The one or more compounds of the bacteria formulation may support viability of the bacteria in situ with the gas or evaporated stomal effluent.

Accordingly, in an embodiment, a bacteria formulation, such as the odor neutralizing bacteria formulation, may replace activated carbon and potassium permanganate (KMnO4) in a conventional pouch filter. Dehydrated bacteria may become reanimated or activated when exposed to gas or evaporated stomal effluent vented through the pouch filter. The bacteria may deodorize the gas or evaporated stomal effluent passing through the pouch filter. Thus, odors typically associated with ostomy pouch venting may be substantially neutralized or avoided.

In an embodiment, the pouch filter may include a filter element and a bacteria formulation, such as the odor neutralizing bacteria formulation. The bacteria formulation may include bacteria, such as odor neutralizing bacteria, and one or more compounds for supporting viability of the bacteria. The pouch filter, for example, the filter element, may include multiple sections, such as multiple layers, compartments or chambers. The multiple sections may be configured to contain different bacteria formulations. For example, the filter element may include a first section and a second section.

The bacteria formulations may include a first bacteria formulation and a second bacteria formulation. In an embodiment, the first bacteria formulation may be provided at the first section and the second bacteria formulation may be provided at the second section.

In an embodiment, the bacteria formulation may be configured to facilitate a reaction. For example, the bacteria used in the bacteria formulation and/or the one or more compounds may be varied to facilitate different reactions. For example, the one or more compounds may include a supporting nutrient which may be varied to facilitate different reactions.

Accordingly, different reactions may be facilitated at different sections of the pouch filter. For example, at the first section, first odor neutralizing bacteria may be provided with selected supporting nutrients to facilitate a first reaction to convert hydrogen sulfide to a neutralized variant. For example, the first bacteria formulation may be configured to provide pH in a range suitable for converting hydrogen sulfide to a neutralized variant. At the second section, second odor neutralizing bacteria may be provided with selected supporting nutrients to facilitate a second reaction to convert methyl mercaptan to a neutralized variant. For example, the second bacteria formulation may be configured to provide pH in a range suitable for converting methyl mercaptan to a neutralized variant.

In an embodiment, the pouch filter, for example, the filter element, may further include a buffer between the sections. In an embodiment, the buffer may maintain a desired pH range for the intended reaction in the different sections.

Alternatively, in an embodiment, the pouch filter may include a bacteria formulation, such as an odor neutralizing bacteria formulation, to convert a selected target gas to a neutralized variant. For example, the pouch filter may be configured to maintain a pH level optimally suited for converting either hydrogen sulfide or methyl mercaptan to a neutralized variant.

In the manner above, an ostomy pouch system having an ostomy pouch with a pouch filter, may be provided having a bacteria formulation, such as the odor neutralizing bacteria formulation. In an embodiment, the pouch filter, for example the filter element, does not include activated carbon and potassium permanganate ($KMnO4$). The bacteria may oxidize hydrogen sulfide H2S, methyl mercaptan CH4S, and/or other odorous gases and/or liquids to deodorize gas or evaporated stomal effluent passing through pouch filter. Such a pouch filter may offer cost savings compared to a conventional ostomy pouch filter, may be environmentally friendly and may more thoroughly convert and remove odorous gases vented from the ostomy pouch.

Alternatively, the pouch filter may include the activated carbon filter element and a bacteria formulation, such as the odor neutralizing bacteria formulation. In an embodiment, the bacteria formulation may be included as an additional layer to supplement the activated carbon layer. In this manner, a deodorizing capacity of the pouch filter may be increased, and less noxious odors may escape the ostomy pouch.

According to an embodiment, a bacteria formulation, such as the odor neutralizing and probiotic bacteria formulation, may be added to a skin contacting adhesive of a medical product. For example, the bacteria formulation may be added to a skin contacting adhesive of an ostomy appliance, a wound care product, a critical care product, a temporary anchor device, a patient monitoring product and the like. In an embodiment, the bacteria formulation may be added, for example, by the manufacturer after manufacture of the skin contacting adhesive or medical product, or later, by user, prior to using the skin contacting adhesive or medical product.

In an embodiment, bacteria, such as the odor neutralizing bacteria and/or the probiotic bacteria, may be provided in a dehydrated form. The bacteria may be rehydrated and become reanimated, for example, in response to exposure to water vapor or moisture from the skin contacting adhesive and/or perspiration from a user's skin.

The bacteria formulation may be provided or packaged, for example, as microbeads prior to incorporation into the skin contacting adhesive. In an embodiment, the bacteria formulation may include separate microbeads for the odor neutralizing bacteria and the probiotic bacteria. Alternatively, the bacteria and the one or more compounds may be blended together to form the microbeads. Alternatively, or in addition, the bacteria formulation may be mixed into the skin contacting adhesive. The one or more compounds of the bacteria formulation may support viability of the bacteria in situ with the environmental materials, such as moisture or water vapor.

Accordingly, in an embodiment, a bacteria formulation, such as the odor neutralizing and probiotic formulation, may be included in a skin contacting adhesive. Dehydrated bacteria may become reanimated or activated, for example, when exposed to moisture, such as perspiration from the user's skin or moisture from the skin contacting adhesive. Bacteria of the formulation, such as the odor neutralizing bacteria, may deodorize body odors originating, for example, from between the skin contacting adhesive and the user's skin. In addition, bacteria of the formulation, such as the probiotic bacteria, may provide an antimicrobial effect at or near the user's skin and may protect against pathogens. Accordingly, skin infections may be inhibited as well.

In the manner above, a skin contacting adhesive of a medical product may be provided having a skin contacting adhesive material and a bacteria formulation, such as the odor neutralizing and probiotic bacteria formulation. The skin contacting adhesive material may include the bacteria formulation. The bacteria formulation may neutralize odors, such as body odors, and may inhibit skin infections, such as bacterial, fungal and/or yeast skin infections.

In an embodiment, an ostomy pouch system may include an ostomy appliance. The ostomy appliance may include the skin contacting adhesive having a bacteria formulation, such as the odor neutralizing and probiotic bacteria formulation. In other embodiments, medical products including the skin contacting adhesive having a bacteria formulation, such as the odor neutralizing and probiotic bacteria formulation, may be, for example, a wound care product, a critical care product, a temporary anchorage device, a patient monitoring product, and other similar medical products configured to adhere to a user's body.

According to an embodiment, a bacteria formulation, such as the odor neutralizing and probiotic bacteria formulation, may be added to a pouch film or comfort panel of an ostomy pouch. In an embodiment, the bacteria formulation may be added during manufacture of the ostomy pouch, i.e., when the film or comfort panel is being made, or as a post manufacturing step.

In an embodiment, bacteria, such as the odor neutralizing bacteria and/or the probiotic bacteria, may be provided in a dehydrated form. The bacteria may be rehydrated and become reanimated, for example, in response to exposure to water vapor or moisture, such as perspiration from the user's skin.

In an embodiment, the bacteria formulation may be provided or packaged as microbeads prior to incorporation with the pouch film or comfort panel. In an embodiment, the bacteria and the one or more compounds may be blended together to form the microbeads. In an embodiment, separate microbeads may be formed for the odor neutralizing bacteria and the probiotic bacteria. Alternatively, or in addition, the bacteria and the one or more compounds may be spun or woven into desired layers of the ostomy pouch, such as the pouch film or comfort panel. The one or more compounds of the bacteria formulation may support viability of the bacteria in situ with the environmental materials, such as moisture or water vapor.

Accordingly, in an embodiment, a bacteria formulation, such as the odor neutralizing and probiotic formulation, may be added to or included in an ostomy pouch, for example, with a pouch film or a comfort panel. Dehydrated bacteria may become reanimated or activated, for example, when exposed to moisture, such as perspiration from the user's skin or water vapor. Bacteria of the formulation, such as the odor neutralizing bacteria, may deodorize body odors originating, for example, from between the ostomy pouch and the user's skin. In addition, bacteria of the formulation, such as the probiotic bacteria, may provide an antimicrobial effect at or near the user's skin and may protect against pathogens. Accordingly, skin infections may be inhibited as well.

In the manner above, an ostomy pouch having a pouch film or a comfort panel may be provided having a bacteria formulation, such as the odor neutralizing and probiotic bacteria formulation. The bacteria formulation be provided at or in the pouch film or comfort panel. The bacteria formulation may neutralize odors, such as body odors, and may inhibit skin infections, such as bacterial, fungal and/or yeast skin infections.

According to an embodiment, a bacteria formulation, such as the odor neutralizing and probiotic bacteria formulation, may be added to a skin fold management fabric. In an embodiment, the bacteria formulation may be added to the skin fold management fabric during manufacture of the fabric, or later, as a post manufacturing step.

In an embodiment, the bacteria, such as the odor neutralizing bacteria and/or the probiotic bacteria, may be provided in a dehydrated form. The bacteria may be rehydrated and become reanimated, for example, in response to exposure to water vapor or moisture, such as perspiration from the user's skin.

In an embodiment, the bacteria formulation may be provided or packaged as microbeads prior to incorporation with the skin fold management fabric. In an embodiment, the bacteria and the one or more compounds may be blended together to form the microbeads. In an embodiment, separate microbeads may be formed for the odor neutralizing bacteria and the probiotic bacteria. Alternatively, or in addition, the bacteria and the one or more compounds may be spun or woven into a desired layer or layers of the skin fold management fabric. The one or more compounds of the bacteria formulation may support viability of the bacteria in situ with the environmental materials, such as moisture or water vapor.

Accordingly, in an embodiment, a bacteria formulation, such as the odor neutralizing and probiotic formulation, may be added to or included in skin fold management fabric. Dehydrated bacteria may become reanimated or activated, for example, when exposed to moisture, such as perspiration from the user's skin or water vapor. Bacteria of the formulation, such as the odor neutralizing bacteria, may deodorize body odors. In addition, bacteria of the formulation, such as the probiotic bacteria, may provide an antimicrobial effect at or near the user's skin and may protect against pathogens. For example, the probiotic bacteria may protect against pathogens which can cause skin infections, including bacterial, fungal and/or yeast skin infections including candidiasis.

In the manner above, a skin fold management fabric, or a product having a skin fold management fabric, may be provided having a fabric material which includes a bacteria formulation, such as the odor neutralizing and probiotic formulation. The bacteria formulation may be provided with the skin fold management fabric, and may neutralize odors, such as body odors, and may inhibit skin infections, such as bacterial, fungal and/or yeast skin infections.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy system comprising:
an ostomy pouch having opposed sidewalls forming an enclosed area configured to receive and store stomal effluent and a pouch filter connected to one of the sidewalls;
an ostomy appliance configured to be adhered to a user's skin; and
a bacteria formulation comprising bacteria including odor neutralizing bacteria and one or more compounds for supporting viability of the bacteria, wherein the bacteria formulation comprises a first bacteria formulation configured to provide pH in a range of 2-3 and a second bacteria formulation configured to provide pH in a range of 6-8;
wherein the pouch filter comprises a filter element comprising a first section and a second section, the first bacteria formulation is provided at the first section, and the second bacteria formulation is provided at the second section.

2. The ostomy system of claim 1, wherein the bacteria formulation is disposed in the enclosed area of the ostomy pouch.

3. The ostomy system of claim 1, wherein the pouch filter includes the bacteria formulation.

4. The ostomy system of claim 3, wherein the pouch filter does not comprise activated carbon.

5. The ostomy system of claim 1, wherein the bacteria further include probiotic bacteria for providing an antimicrobial effect.

6. The ostomy system of claim 5, wherein the ostomy pouch comprises a pouch film which includes the bacteria formulation.

7. The ostomy system of claim 5, wherein the ostomy pouch comprises a comfort panel which includes the bacteria formulation.

8. The ostomy system of claim 5, wherein the ostomy appliance comprises a skin contacting adhesive which includes the bacteria formulation.

9. The ostomy system of claim 1, wherein the odor neutralizing bacteria are one or more of: *Thiobacillus* sp., *Thiobacillus denitrificans, Thiobacillus ferrooxidans, Thiobacillus thiooxidans, Thiobacillus novellus, Thiobacillus thioparus, Thermothrix azorensis, Thiothrix nivea, Thioalkalispira microaerophila* and *Thiomicropira frisia*.

10. The ostomy system of claim 5, wherein the probiotic bacteria are one or more of: *Lactobacillus* spp, *Lactococcus, Leuconostoc, Bifidobacterium* and *Saccharomyces*.

11. The ostomy system of claim 1, wherein the first bacteria formulation is configured to convert hydrogen sulfide to a neutralized variant and the second bacteria formulation is configured to convert methyl mercaptan to a neutralized variant.

12. The ostomy system of claim 1, wherein the one or more compounds for supporting viability of the bacteria include one or more of a nutrient, a buffering agent and/or a supplement.

13. The ostomy system of claim 1, wherein the bacteria formulation further comprises photosynthetic bacteria.

14. The ostomy system of claim 1, wherein the bacteria formulation further comprises *Beggiatoa* spp.

\* \* \* \* \*